United States Patent [19]
Friedman et al.

[11] Patent Number: 5,147,355
[45] Date of Patent: Sep. 15, 1992

[54] CRYOABLATION CATHETER AND METHOD OF PERFORMING CRYOABLATION

[75] Inventors: Peter L. Friedman, Rowley; Paul Wang, Brookline; Ernest G. Cravalho, Wellesley Hills, all of Mass.

[73] Assignee: Brigham and Womens Hospital, Boston, Mass.

[21] Appl. No.: 249,343

[22] Filed: Sep. 23, 1988

[51] Int. Cl.$^5$ .............................................. A61B 17/36
[52] U.S. Cl. ........................................ 606/23; 606/21
[58] Field of Search ................................. 606/20–26; 128/303.1, 362, 399–401, DIG. 27; 604/113

[56] References Cited

U.S. PATENT DOCUMENTS

| | | | |
|---|---|---|---|
| 3,272,203 | 9/1966 | Chato | 606/26 |
| 3,298,371 | 1/1967 | Lee | 606/23 |
| 3,393,679 | 7/1968 | Crump et al. | 606/26 |
| 3,425,419 | 2/1969 | Dato | 606/22 |
| 3,512,531 | 5/1970 | Crump et al. | 606/26 |
| 3,548,829 | 12/1970 | Reynolds et al. | |
| 3,644,344 | 5/1972 | Bryne | |
| 3,823,718 | 7/1974 | Tromovitch | |
| 3,859,986 | 1/1975 | Okada et al. | 606/20 X |
| 3,910,277 | 10/1975 | Zimmer | |
| 3,971,383 | 7/1976 | von Gerven | 606/23 |
| 4,029,102 | 6/1977 | Barger | |
| 4,202,336 | 5/1980 | Van Gerven | 606/21 |
| 4,207,897 | 6/1980 | Lloyd et al. | |
| 4,275,734 | 6/1981 | Mitchiner | 606/23 |
| 4,278,090 | 7/1981 | Van Gerven | 606/23 |
| 4,406,656 | 9/1983 | Hattler et al. | |
| 4,519,389 | 5/1985 | Gudkin et al. | |
| 4,860,744 | 8/1989 | Johnson et al. | 606/21 X |

FOREIGN PATENT DOCUMENTS

| | | |
|---|---|---|
| 2731651 | 1/1979 | Fed. Rep. of Germany |
| 2477406 | 3/1980 | France |
| 86/000232 | 1/1986 | PCT Int'l Appl. |
| 532976 | 10/1978 | U.S.S.R. |
| 2226497 | 4/1990 | United Kingdom |

OTHER PUBLICATIONS

Frigitronics CCS-100 Cardiac Cryosurgical System Frigitronics of Connecticut Incorporated, May 1984.

Primary Examiner—John D. Yasko
Assistant Examiner—Adam J. Cermak
Attorney, Agent, or Firm—Sterne, Kessler, Goldstein & Fox

[57] ABSTRACT

A method and apparatus is provided for cryogenically ablating a predetermined portion of tissue in the body of a patient. Cryoablation is accomplished by a cryoablation catheter having a hollow shaft insertable into the blood vessel of a patient. The shaft has a closed tip portion and a fluid flow passage for directing a flow of cryogenic fluid to the tip. Cryogenic cooling is effected by a liquid-to-gas fluid phase change adjacent the catheter tip. Electrical signal activity may be monitored by an electrode formed integral with the tip to confirm treatment of the paper tissue site.

6 Claims, 2 Drawing Sheets

CRYOABLATION CATHETER AND METHOD OF PERFORMING CRYOABLATION

BACKGROUND OF THE INVENTION

1. Field of the Invention

The present invention pertains to catheters, and more particularly to catheters for cryosurgically treating tissue within the body of a patient.

2. Description of the Related Art

Cryosurgery has achieved wide acceptance in many fields of therapeutic medicine. For example, cryosurgical instruments have been used in the extraction of cataractous lenses of the eye, to freeze human tissue to effect necrosis, to form scar tissue, and to repair detached retinas. Examples of cryosurgical instruments are disclosed in U.S. Pat. Nos. 3,548,829; 2,664,344; and 4,039,102.

In recent years, cryosurgery has been employed to ablate particular regions of the heart during open heart surgery. Once the chest cavity of a patient has been opened to expose the heart, a hand-held cryoprobe is advanced to a particular region of the heart believed to be the cause of certain cardiac abnormalities such as arrhythmia. A super-cooled fluid is passed to the tip of the probe to destroy by rapid freezing the abnormal tissue adjacent the probe tip. Such cryosurgical treatment is advantageous because it permits localized and highly specific tissue treatment. However, it can only be used during the course of open heart surgery. Despite recent advances, such open heart surgery is associated with considerable morbidity and mortality.

The management of patients with cardiac arrhythmia has posed a vexing clinical problem. Despite the recent introduction of several powerful anti-arrhythmic drugs, many arrhythmias for reasons yet unknown cannot be suppressed pharmacologically. Patients who do not respond to drug therapy develop an alarmingly high incidence of serious drug-induced side effects and are faced with the inconvenience and expense of taking medication several times a day. Alternative forms of antiarrhythmic therapy which have been recently developed, such as using pacemakers capable of terminating tachycardia, have proven successful in only a limited number of patients. Surgical ablation of some cardiac arrhythmias is also possible in some patients. However, this technique of treatment is associated with considerable morbidity and mortality due to the use of general anesthesia and cardiopulmonary bypass. Consequently, there is a need for a less surgically invasive, more acceptable form of treatment.

Since many cardiac arrhythmias arise from discrete, easily definable regions of the heart that are readily accessible during the course of cardiac catheterization, attention has recently turned to the possibility of ablating arrhythmogenic foci non-surgically using catheterization techniques. Delivery of high-energy DC electric shocks through intracardiac electrode catheters positioned fluoroscopically near the His bundle has been used successfully to produce A-V block in patients having rapid ventricular rates during refractory atrial fibrillation, atrial flutter or other supra-ventricular tachycardias. This same technique has been used to ablate accessory A-V pathways near the mouth of the coronary sinus in some patients suffering from Wolff-Parkinson-Wright syndrome. Unfortunately, the delivery of such high energy intracardiac shocks produces tissue damage that cannot be graded or accurately confined to a small area. This tissue damage may result in serious complications in some patients, and may even produce new arrhythmogenic foci.

Accordingly, it is an object of the present invention to provide a treatment for cardiac arrhythmias that is not accompanied by the problems attendant to previous forms of treatment.

It is another object of the present invention to provide a treatment for cardiac arrhythmias which is comparatively less invasive than other forms of treatment.

Yet another object of the present invention is to provide a treatment for cardiac arrhythmias that permits the identification and highly specific cyrogenic treatment of abnormal cardiac tissue.

Still yet another object of the present invention is to provide a catheter capable of ablating abnormal tissue located virtually anywhere in the body of a patient that is accessible through the circulatory system.

SUMMARY OF THE INVENTION

The present invention provides a method and apparatus for cyrogenically ablating a predetermined portion of tissue in the body of a patient. The apparatus comprises a catheter having a hollow shaft insertable into a blood vessel of the patient. The shaft includes a closed tip portion and a fluid flow passage. Means is provided for coupling the fluid flow passage to a source of cryogenic fluid to provide a flow of cryogenic fluid to the tip of the catheter shaft.

In a further aspect of the invention, means adjacent the tip is provided for effecting a liquid-to-gas phase change in the cryogenic liquid to effect cooling of the tip. Controlling means remote from the tip governs the rate at which the cryogenic fluid phase change occurs. Preferably, a second fluid flow passage is provided to remove gas from the tip, the fluid flow passages being arranged concentrically adjacent the tip. In a preferred embodiment, the phase change is effected by a Joule-Thomson valve positioned adjacent an end of one of the fluid flow passages. Electrical signal sensing means formed integrally with the catheter may be provided to detect electrical signal activity from a predetermined portion of the body of the patient, such as the tissue adjacent the tip of the catheter. The flow of cryogenic fluid to the tip portion is controllable to provide reversible cooling of the tissue adjacent the tip portion to prevent irreversible tissue damage. The preferred cryogenic fluid is liquid nitrous oxide.

In the method of the invention, a catheter having a closed tip portion is inserted into a blood vessel of a patient. The catheter is guided to a predetermined portion of the patient's body and is positioned so that the tip is adjacent the tissue to be ablated. A flow of cyrogenic fluid is directed to the tip and a liquid-to-gas phase change in the cryogen is effected thereat. The preferred cryogenic fluid is nitrous oxide. The gaseous nitrous oxide is removed from the tip. Means such as a valve remote from the catheter tip controls the flow of cyrogenic fluid to the tip to vary the temperature and rate of cooling of the tip. Electrical activity from a predetermined portion of the patient's body may be sensed substantially simultaneously with tissue ablation by an electrode integral with the tip.

BRIEF DESCRIPTION OF THE DRAWINGS

The foregoing and other objects, aspects, uses and advantages of the present invention will be more fully appreciated as the same become better understood from the following detailed description of the present invention when considered in connection with the accompanying drawings, in which.

DETAILED DESCRIPTION OF THE PREFERRED EMBODIMENTS

Figure 1:
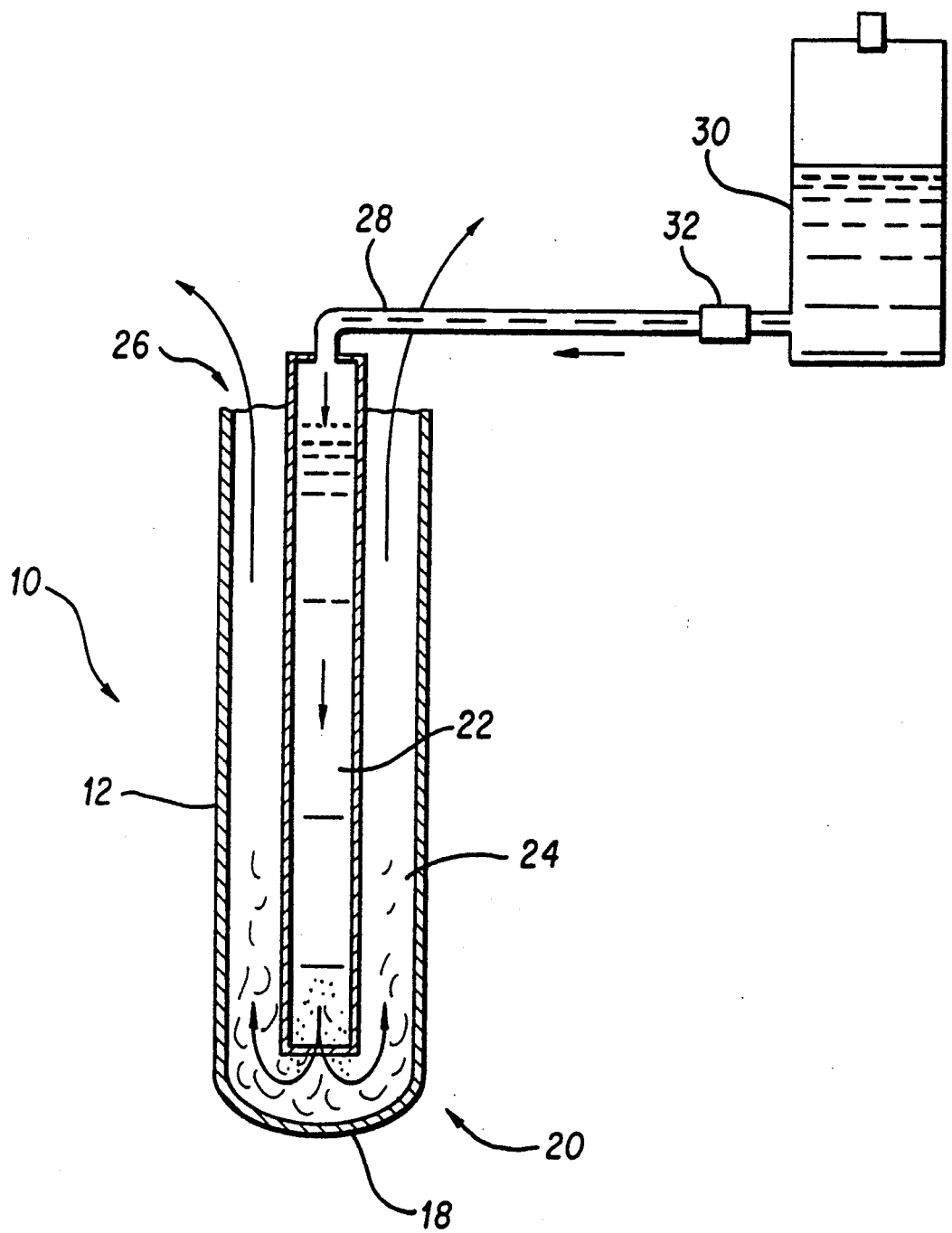
FIG. 1 is a schematic illustration of the catheter of the present invention in cross-section.

Referring now to the drawing figures, wherein like reference numerals represent identical or corresponding parts throughout the several views, a cryoablation catheter denoted generally at 10 includes a catheter 12 insertable into a blood vessel 14 of a patient 16. The distal end 18 of the portion of the catheter shaft 12 that is insertable into the blood vessel is closed to provide a closed tip portion 20.

Catheter shaft 12 includes first and second fluid flow passages 22, 24 that are preferably arranged in a concentric manner adjacent the tip portion 20 of the shaft 12. The flow passages 22, 24 are preferably formed from a material such as stainless steel that is capable of withstanding the high pressures and low temperatures attendant to the handling of a liquid-to-gas phase change in a cryogenic fluid. Details of the phase change are provided below. In the preferred embodiment, the flow passages 22, 24 are formed from a pair of concentric, annealed thin-walled stainless steel tubes approximately 1 mm and 3 mm, respectively, in diameter. Outer fluid flow passage 24 is vented to the atmosphere adjacent the proximal end 26 of the catheter shaft 12. Alternatively, outer flow passage 24 may be coupled to the source 30 of cryogenic fluid to provide a closed system for the return of gaseous N₂O for reprocessing into liquid form. The cryogenic liquid source 30 is coupled via conduit 28 to the inner fluid flow passage 22 of the catheter shaft 12 through a flow control valve 32. Flow control valve 32 may be modulated to regulate the amount of cryogenic liquid delivered to the catheter tip 20, and therefore the temperature and rate of tip cooling.

Cryogenic cooling occurs adjacent the catheter tip 20 as a result of a liquid-to-gas phase change that takes place in the cryogenic fluid. A cryogenic fluid such as liquid nitrous oxide is supplied under pressure to a Joule-Thomson valve 34 positioned adjacent the distal end 36 of the inner fluid flow passage 22. The Joule-Thomson valve 34 effects the phase change by directing the pressurized fluid to the tip 20 of the catheter, where it undergoes rapid expansion and transformation into a gaseous state. This transformation is accompanied by rapid and extreme cooling, as temperatures as low as −60° C. can be attained. The gas is conducted away from the tip 20 through the outer fluid flow passage 24 and is vented to the atmosphere or recycled to the source 30, as discussed above. The tip 20 is preferably formed from any suitable material having a high coefficient of thermal conductivity, such as silver, gold and platinum.

Figure 2:
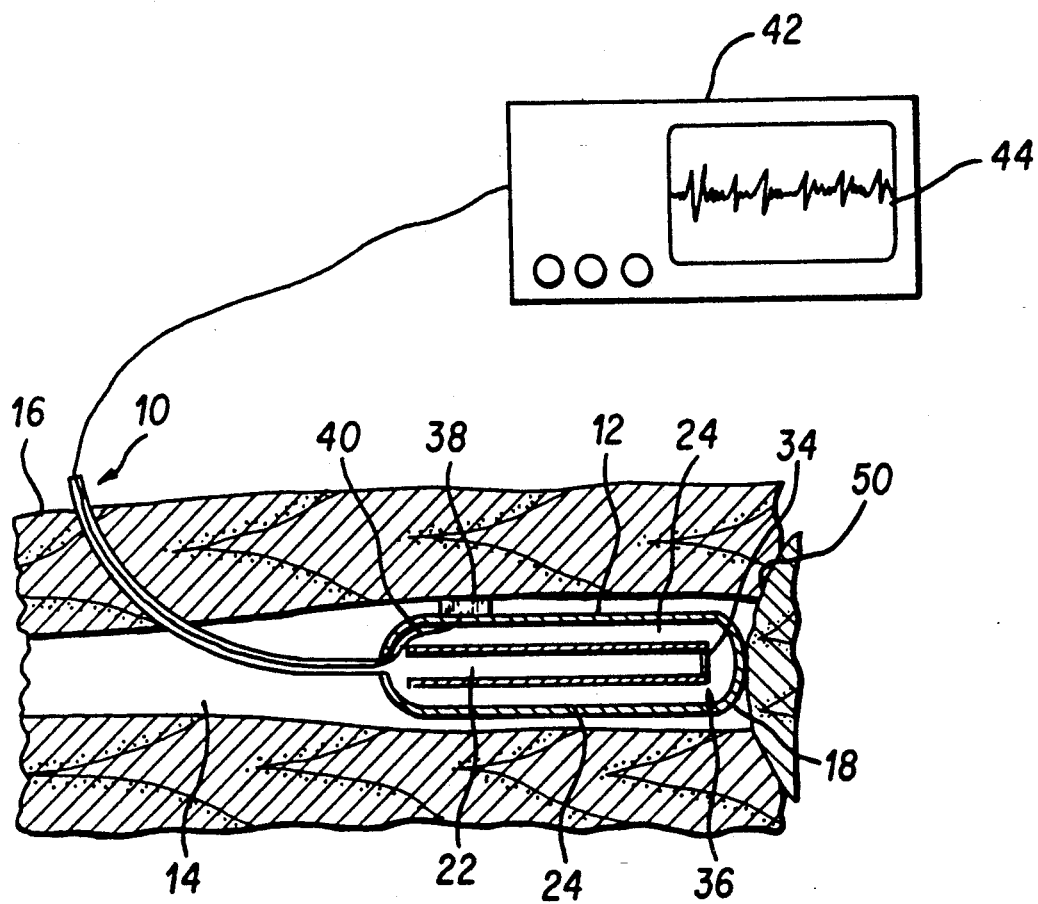
FIG. 2 is a schematic illustration of the catheter of the present invention in use in the body of a patient.

With particular reference to FIG. 2, the cryoablation catheter 10 is depicted positioned in a blood vessel 14 of a patient 16. The tip 20 of the catheter is positioned into abutment with the predetermined portion of tissue 50 selected for ablation.

The arrhythmogenic foci of cardiac arrhythmeia are particularly well suited for ablation in accordance with the present invention, as they are readily identifiable and accessible via catheterization techniques. The catheter 10 is typically guided around anatomical curves to its target tissue through the use of conventional radioimaging techniques such as fluoroscopy. Delivery of the catheter to the tissue 50 to be ablated is facilitated through the monitoring of electrical signal information provided by an electrode 38 positioned adjacent the catheter tip 20. A wire 40 extends from the electrode 38 to a signal monitor 42 having a display 44 for displaying the signal activity detected by the electrode. As cryoablation of the tissue 50 proceeds, changes in the electrical environment surrounding the catheter may be detected by an electrode 38. While the principal use of the electrical signal is to locate the tissue to be ablated, another use may be to monitor changes in the electrical environment surrounding the catheter at tissue 50, in order to provide an indication of the effectiveness of cryoablation and whether the proper tissue has been treated. For example, if during the course of cryoablation an arrhythmic signal continues to be detected by the electrode 38, the flow of cryogenic liquid to the catheter tip 20 may be terminated so as to curtail ablation of the tissue adjacent the tip. Normal tissue temperature will be restored by the flow of blood thereby. The catheter tip 20 may then be re-positioned to cryogenically ablate another section of tissue suspected as being the source of the abnormality for which treatment is sought. A desirable signal display 44 following tissue cryoablation confirms targeting of the abnormal tissue and the effectiveness of the treatment.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing detailed description should be considered exemplary in nature and not limited to the scope and spirit of the invention as set forth in the attached claims.

What is claimed is:

1. A method of cryogenically ablating a predetermined portion of tissue within a blood vessel of a patient, comprising the steps of:

inserting a catheter having a tip portion into the lumen of the blood vessel;

guiding said catheter to a predetermined portion of the patient's body and positioning said tip portion adjacent tissue within the lumen of the blood vessel to be ablated;

directing a flow of cryogenic fluid to said tip portion;

effecting a cooling of said cryogenic fluid adjacent said tip portion; and removing said fluid from said tip portion.

2. A method according to claim 1, wherein said step of directing said flow of cryogenic fluid comprises directing said fluid to said catheter tip through a first fluid flow passage formed in said catheter and said step of removing said fluid comprises directing said fluid through a second fluid flow passage formed in said catheter.

3. A method according to claim 1, further comprising the step of controlling said flow of cryogenic fluid remote from said catheter tip to vary the temperature and rate of cooling of said tip portion.

4. A method according to claim 3, further comprising the step of throttling said flow of cryogenic fluid to provide reversible cooling of said tissue adjacent said catheter tip portion.

5. A method according to claim 1, further comprising the step of sensing electrical activity from said predetermined portion of the body with a device integral with said tip.

6. A method according to claim 5, wherein the steps of sensing said electrical activity and ablating said tissue occur substantially simultaneously.

* * * * *